United States Patent [19]

Hirth

[11] Patent Number: 4,621,229

[45] Date of Patent: Nov. 4, 1986

[54] INSTRUMENT FOR MEASURING THE MOISTURE CONTENT OF SOLIDS

[75] Inventor: Friedrich Hirth, Stuttgart, Fed. Rep. of Germany

[73] Assignee: Gann Mess- U. Regeltechnik GmbH, Stuttgart, Fed. Rep. of Germany

[21] Appl. No.: 640,382

[22] Filed: Aug. 13, 1984

[51] Int. Cl.⁴ .................................... G01R 27/02
[52] U.S. Cl. ........................................ 324/65 R
[58] Field of Search ................ 324/65 R, 63, 61 R

[56] References Cited

U.S. PATENT DOCUMENTS

| | | | |
|---|---|---|---|
| 3,609,549 | 9/1971 | Hausler et al. | 324/65 R X |
| 4,019,132 | 4/1977 | Loch | 324/65 R |
| 4,041,382 | 8/1977 | Washburn | 324/63 X |
| 4,408,128 | 10/1983 | Fujita | 324/65 R |

FOREIGN PATENT DOCUMENTS

| | | | |
|---|---|---|---|
| 1101011 | 1/1968 | United Kingdom | 324/65 R |
| 1122038 | 7/1968 | United Kingdom | 324/65 R |
| 0576534 | 10/1977 | U.S.S.R. | 324/65 R |

Primary Examiner—Stanley T. Krawczewicz
Attorney, Agent, or Firm—Peter K. Kontler

[57] ABSTRACT

An instrument for measuring the moisture content of solids has probes which are placed in contact with a material undergoing moisture determination in order to measure the electrical resistance of the material. A d.c. voltage source is connected with the probes and generates the voltage required for measurement of the electrical resistance. The characteristic line representing the electrical resistance of the material as a function of its moisture content is logarithmic in nature and, in order to generate a straight characteristic line, the signals from the probes are fed to a logarithmic amplifier. The amplified signals are converted to a moisture content which may be read from an indicator constituting part of the instrument. A calibrating unit is interposed between the logarithmic amplifier and the indicator and functions to adjust the characteristic line of the instrument so that this at least approximates the characteristic line of the material undergoing moisture determination.

17 Claims, 3 Drawing Figures

INSTRUMENT FOR MEASURING THE MOISTURE CONTENT OF SOLIDS

BACKGROUND OF THE INVENTION

The invention relates generally to an instrument for moisture determination.

More particularly, the invention relates to an electrical instrument for measuring the moisture content of granular solids, e.g. grain, as well as non-granular solids such as, for example, wood, hardened or set structural materials, and insulating materials.

A known electrical instrument for determining the moisture content of a material functions to measure the electrical resistance of the material. The electrical resistance is converted into a moisture reading. The instrument has a sensor which is contacted with the material in order to measure the electrical resistance of the latter. The instrument is further provided with a suitable indicator for indicating the moisture content of the material. An amplifier, and preferably a logarithmic amplifier, is disposed between the sensor and the indicator to amplify the signals transmitted by the sensor. Furthermore, a calibrating circuit is located between the amplifier and the indicator. The calibrating circuit, which functions to adjust the instrument to the particular material being measured, includes a potentiometer which is connected with the output of the amplifier. The output or tap of the potentiometer is connected with the indicator. Advantageously, a second amplifier is disposed between the potentiometer and the indicator. The potentiometer is adjustable from externally of the instrument.

As indicated above, the amplifier which is connected with the input of the potentiometer is preferably a logarithmic amplifier. The reason is that the characteristic curve representing the absolute moisture content of the material as a function of the electrical resistance is logarithmic in nature. By using a logarithmic amplifier, the signals generated by the sensor are thus converted to a linear function over a wide range of values, i.e. the characteristic curve becomes linear over a wide range of values.

The characteristic line representing the absolute moisture content as a function of the measured resistance is different for different types of materials and also for different materials of the same type. For example, the characteristic lines for grain and wood are different. In addition, the characteristic lines for different forms of grain are different as are the characteristic lines for different forms of wood such as pine, beech, and so on.

The calibrating circuit outlined above makes it possible to measure the moisture content of different materials, e.g. different forms of wood, with a single instrument. To this end, the calibrating circuit enables the moisture measuring instrument to operate along a series of characteristic lines. In this manner, the instrument may at least approximate the individual characteristic lines of the different forms of a particular type of material.

The potentiometer of the calibrating circuit operates to effect a proportional change in the readings of the measuring instrument and thereby causes the slope of the characteristic line of the instrument to change. This permits a first approximation to the characteristic line of a given material to be achieved. However, a first approximation is inadequate in many instances. Thus, the range of adjustment obtainable through a change in slope is not sufficiently wide to take into account all different forms of a particular type of material, and the characteristic lines of certain forms may lie relatively far outside of the adjustment range so that the approximation by the measuring instrument is relatively poor. The situation is even worse when the instrument is to approximate the characteristic lines of different types of materials, e.g. grain and wood, because the deviation of the characteristic lines of different types of materials from an average range or field of characteristic lines is greater than that for different forms of the same type of material. In addition, the characteristic lines for different types of materials may have a different appearance.

OBJECTS AND SUMMARY OF THE INVENTION

It is an object of the invention to provide a moisture measuring instrument which is capable of operating along a larger number of characteristic lines than the instruments of the prior art.

Another object of the invention is to provide a moisture measuring instrument which is capable of approximating the characteristic lines of different materials more closely than the instruments of the prior art.

An additional object of the invention is to provide an electrical moisture measuring instrument of the type described above which is capable of operating along a larger number of characteristic lines, and is capable of being more precisely adjusted to the characteristic lines of different materials, than the corresponding instruments of the prior art.

The preceding objects, and others which will become apparent as the description proceeds, are achieved by the invention.

A moisture measuring instrument according to the invention comprises the following:

(a) A sensor for contacting a material undergoing moisture determination. The sensor is preferably designed to sense the electrical resistance or electrical conductivity of the material.

(b) An indicator for indicating the moisture content of the material. The indicator may take any suitable form such as a dial or a digital read-out.

(c) A calibrating unit or circuit between the sensor and the indicator designed to calibrate the instrument for different materials. The calibrating unit includes a calibrating voltage source as well as a summing device having output means connected with the indicator and input means The calibrating unit further includes a first voltage adjusting device having a first input connected with the sensor and a first output connected with the input means of the summing device The calibrating unit additionally includes a second voltage adjusting device having a second input connected with the calibrating voltage source and a second output connected with the input means of the summing device. The voltage adjusting devices, which may be in the form of potentiometers, are preferably operable from externally of the instrument. The summing device advantageously comprises or is constituted by an amplifier.

An amplifier may also be disposed between the sensor and the calibrating unit. This amplifier is preferably a logarithmic amplifier due to the fact that the characteristic curve representing the moisture content of a material as a function of its electrical resistance is logarithmic in nature.

The instrument of the invention is particularly well-suited for measuring the moisture content of granular and non-granular solids including grain, wood and hardened or set structural materials.

Similarly to the instruments of the prior art, the instrument according to the invention permits the voltage representing the moisture content of a material, and hence the slope of the characteristic line, to be changed. In addition, however, the instrument in accordance with the invention makes it possible to shift the entire characteristic line parallel to itself by a certain distance to either side. In other words, the instrument according to the invention permits the characteristic line to be shifted to a new position which is spaced from but parallel to its original position. It may be readily seen that this enables the instrument of the invention to be adjusted to many more characteristic lines than heretofore, and also enables the instrument of the invention to approximate the characteristic lines of different materials more closely than the instruments of the prior art.

The direction and magnitude of the shift of the characteristic line parallel to itself are determined by the voltage of the calibrating voltage source, and the voltage differential between this source and the input of the calibrating unit, i.e. the voltage differential between the calibrating voltage source and the output of the amplifier disposed intermediate the sensor and the calibrating unit. It is possible, for example, to select the calibrating voltage source in such a manner that the characteristic line may be shifted by the same amount in either a positive or negative direction about a middle value of zero. Another possibility is to select the calibrating voltage source so that the characteristic line may be shifted parallel to itself in only one of these directions. It is further possible to select the calibrating voltage source in such a manner that the zero value for the characteristic line is located between the midpoint of the voltage range of the potentiometer connected with the calibrating voltage source and one of the end points of this range. This enables the characteristic line to be shifted by a larger amount in one direction than in the other.

According to one embodiment of the invention, the summing device is in the form of an inverting operational amplifier and the outputs or taps of both potentiometers are connected with the inverting input of this amplifier. The calibrating unit is then particularly simple and inexpensive. Thus, the inverting operational amplifier functions both to add the output voltages of the potentiometers and to amplify the resulting voltage signal which activates the indicator.

As mentioned previously, the potentiometers are preferably operable from externally of the instrument. To this end, the moisture measuring instrument may be provided with external adjusting knobs or the like for manipulating the tape of the potentiometers. By providing a series of digits or other suitable symbols on or adjacent to the knob for each potentiometer, it becomes possible to program the instrument with specific characteristic lines, e.g. by assigning each characteristic line one digit from each knob so that a given characteristic line is automatically obtained when the respective knobs are set to the corresponding digits. The two potentiometers may be adjustable independently of one another. However, it is also possible to design the potentiometers so that the taps may be locked to one another in a predetermined relationship and adjusted in unison.

According to another embodiment of the invention, the calibrating unit or circuit includes temperature compensation means to correct for temperature so that a corrected or standardized moisture content is obtained regardless of the temperature of a material at the time of moisture determination. This is of advantage, for example, in the drying of wood.

The novel features which are considered as characteristic of the invention are set forth in particular in the appended claims. The improved moisture measuring instrument itself, however, both as to its construction and its mode of operation, together with additional features and advantages thereof, will be best understood upon perusal of the following detailed description of certain specific embodiments when read in conjunction with the accompanying drawings.

DESCRIPTION OF THE PREFERRED EMBODIMENTS

Figure 1:
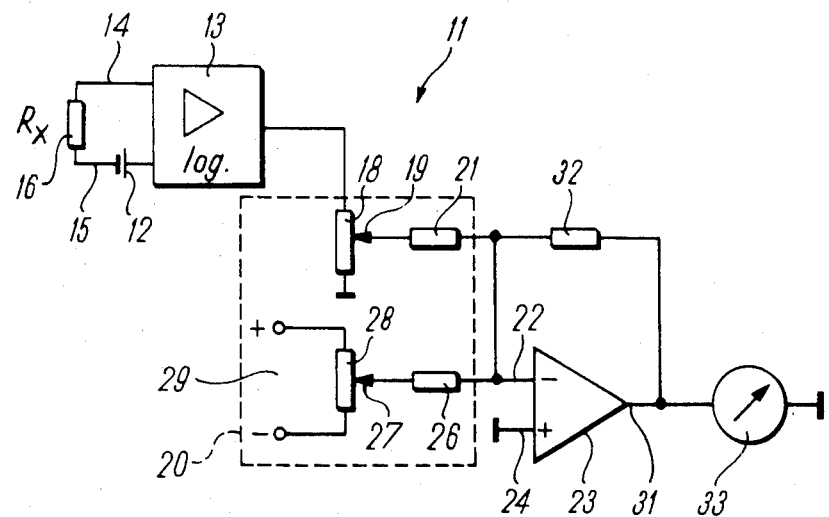
FIG. 1 illustrates one embodiment of a moisture measuring instrument according to the invention.

Referring to FIG. 1, the reference numeral 11 generally identifies an electrical moisture measuring instrument according to the invention. The instrument 11 is designed to measure the moisture content of all types of solids including granular solids such as, for example, grain, as well as non-granular solids. Examples of non-granular solids which may undergo moisture determination by the instrument 11 are hardened or set structural materials, insulating materials and wood.

The instrument 11 has a calibrating unit which comprises a circuit 20 and an inverting operational amplifier 23. The circuit 20 is operable from externally of the instrument 11, e.g. by means of non-illustrated knobs or dials. For any given material, the calibrating unit 20,23 enables the measured characteristic line, i.e. the characteristic line along which the electrical moisture measuring instrument 11 operates, to be adjusted to the characteristic line of the material in an optimum manner. In other words, the calibrating unit 20,23 makes it possible to change the slope of the characteristic line of the instrument 11 and, in addition, to shift the characteristic line parallel to itself so as to achieve the closest possible approximation of the characteristic line of the instrument 11 to the characteristic line of the material undergoing moisture determination.

The electrical moisture measuring instrument 11 operates to measure the electrical resistance or electrical conductivity of a material. The measured resistance or conductivity is then converted into a moisture content.

In FIG. 1, the material undergoing moisture determination is identified by the reference numeral 16 and is assumed to have a resistance $R_x$. The instrument 11 has a pair of conductors or probes 14 and 15 which are placed in contact with the material 16 in order to determine the moisture content thereof. The probes 14 and 15 together constitute a sensor which is here assumed to measure the electrical resistance $R_x$ of the material 16. If the material 16 undergoing moisture determination is wood, the probes 14 and 15 may, for instance, comprise or be constituted by metallic pins which are designed to be driven into the wood. On the other hand, if the material 16 is a granular material such as grain, the material 16 may, for example, be confined in a measuring vessel and the probes 14,15 inserted in the vessel.

The probes 14 and 15 are connected with respective inputs of an amplifier 13. The amplifier 13 is preferably a logarithmic amplifier as shown since the characteristic line representing the absolute moisture content of the material 16 as a function of its resistance $R_x$ is logarithmic in nature. A source 12 of measuring voltage is interposed in the probe 15 or between the latter and the associated input of the logarithmic amplifier 13. The measuring voltage source 12, which is here a d.c. voltage source, serves to generate the voltage required for measurement of the resistance $R_x$ of the material 16.

The output of the amplifier 13 is connected with a first potentiometer or first voltage adjusting device 18 constituting part of the circuit 20 of the calibrating unit 20,23. In addition to the amplifier 13, the potentiometer 18 is connected with a source of fixed potential, e.g. ground. The current which issues from the output of the logarithmic amplifier 13 flows through and causes a specific voltage drop to occur in the potentiometer 18.

The potentiometer 18 has a tap 19 which is adjustable from externally of the moisture measuring instrument 11, e.g. by means of a non-illustrated rotary knob. The tap 19 is connected with a resistor 21 which, in turn, is connected with an inverting input 22 of the inverting operational amplifier 23 constituting part of the calibrating unit 20,23. The resistor 21 likewise forms part of the calibrating unit 20,23. The operational amplifier 23 has a non-inverting input 24 which is connected with a source of fixed potential, e.g. ground.

The operational amplifier 23 constitutes or forms part of a summing device.

The circuit 20 of the calibrating unit 20,23 further includes a second potentiometer or second voltage adjusting device 28 having a tap 27. The tap 27 is again operable from externally of the instrument 11, e.g. via a non-illustrated rotary knob. The tap 27 is connected with a resistor 26 and the latter is, in turn, connected with the inverting input 22 of the operational amplifier 23. The resistor 26 also forms part of the calibrating unit 20,23.

The circuit 20 additionally comprises an auxiliary or calibrating voltage source 29 which is here a d.c. voltage source. The potentiometer 28 is connected with the two terminals of the calibrating voltage source 29.

As mentioned previously, the calibrating unit 20,23 makes it possible to shift the characteristic line of the measuring instrument 11 parallel to itself. The direction and maximum amount of the shift are a function of the voltage of the source 29 and the difference between the voltage of the source 29 and the output voltage of the logarithmic amplifier 13. Thus, the direction and maximum amount of the shift of the characteristic line parallel to itself may be regulated by appropriate selection of the voltage of the source 29 and the difference between this voltage and the output voltage of the amplifier 13. It will be observed that the output voltage of the logarithmic amplifier 13 represents the input voltage of the calibrating unit 20,23.

The operational amplifier 23 has an output 31. The output 31 is connected with the inverting input 22 of the operational amplifier 23 via a feedback circuit including a resistor 32. The output 31 of the operational amplifier 23 is further connected with an indicator 33 which provides a reading of the moisture content of the material 16. The indicator 33 is grounded.

Although not illustrated in FIG. 1, a voltage is provided for the amplifier 23 in a conventional manner.

Figure 2:
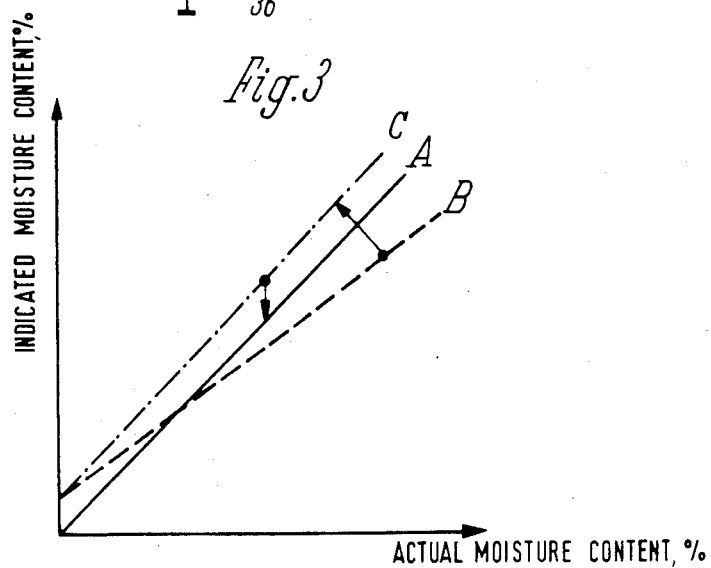
FIG. 2 is a plot of actual moisture content versus indicated moisture content illustrating the shift in a characteristic line obtainable with the instrument of FIG. 1.

FIG. 2 shows a Cartesian coordinate system in which the indicated moisture content of the material 16 in percent, i.e. the moisture content of the material 16 as read from the indicator 33, is plotted as a function of the actual moisture content of the material 16 in percent. It will be recalled that the indicated moisture content of the material 16 is derived from the resistance $R_x$ of the latter. FIG. 2 illustrates how the characteristic line of the measuring instrument 11 may be adjusted so as to at least approximate the characteristic line of the material 16 when measuring the moisture content of granular and non-granular solids such as, for example, grain and wood.

For the purpose of explanation, it is assumed in FIG. 2 that the material 16 undergoing moisture determination is an object composed of a specific type of wood. The characteristic line of the material 16 is denoted by the reference character A while the characteristic line of the measuring instrument 11 prior to adjustment is denoted by the reference character B.

In order to bring the characteristic line B of the instrument 11 into closer conformance with the characteristic line A of the material 16, the tap 19 of the potentiometer 18 is adjusted. Adjustment of the tap 19 effects a proportional change in voltage. As a result, the readings of the indicator 33 are changed. This is accompanied by a change in slope of the characteristic line B of the instrument 11. The tap 19 is adjusted in such a manner that the slope of the characteristic line B becomes equal or approximately equal to the slope of the characteristic line A of the material 16. The position of the characteristic line B of the instrument 11 after adjustment of the tap 19 is denoted by the line C. The displacement of the characteristic line B during adjustment of the tap 19 is indicated by the arrow bc.

The tap 27 of the potentiometer 28 is adjusted also. This causes a change in the voltage which is supplied to the inverting input 22 of the operational amplifier 23 from the calibrating voltage source 29. The operational amplifier 23 adds the voltage from the source 29 to the output voltage of the potentiometer 18 which, in turn, is a function of the voltage generated during measurement of the resistance $R_x$ of the material 16. Thus, by adjusting the tap 27 of the potentiometer 28 and thereby changing the output voltage of the latter which is due to the calibrating voltage source 29, the sum of the voltages supplied to the inverting input 22 of the operational amplifier 23 is changed by a predetermined amount. A change in the sum of the voltages supplied to the inverting input 22 corresponds to a parallel shift, i.e. to a shift parallel to itself, of the characteristic line represented by the voltages at the output 31 of the operational amplifier 23. Stated differently, a change in the sum of the voltages supplied to the inverting input 22 causes the characteristic line to shift to a new position which is spaced from but parallel to its original position. In the example of FIG. 2, the tap 27 of the potentiometer 28 is adjusted in such a manner that the line C is shifted parallel to itself in a negative direction towards the characteristic line A of the material 16. The displacement of the line C during adjustment of the tap 27 is indicated by the arrow ca. A shift of the line C in a negative direction is achieved by adjusting the tap 27 so that a positive voltage change occurs, i.e. so that the voltage increases. A negative voltage change or voltage decrease, on the other hand, would cause the line C to shift parallel to itself in a positive direction, that is, upwards as viewed in FIG. 2.

It is thus possible to calibrate the measuring instrument 11 by adjusting the characteristic line B thereof so that it closely approximates or is superimposed upon the characteristic line A of the particular material 16 undergoing moisture determination.

The measuring instrument 11 of the invention enables the characteristic lines of the most diverse materials to be at least closely approximated. This is a result of the fact that the measuring instrument 11 makes it possible not only to change the slope of a characteristic line obtained with specific instrument parameters but also to shift this characteristic line parallel to itself.

As mentioned earlier, the taps 19,27 of the potentiometers 18,28 may be operable from externally of the measuring instrument 11. If the taps 19,27 are adjustable independently of one another and different positions of each of the taps 19,27 are identified by respective numerals, the most diverse characteristic lines, e.g. for different types of wood and different types of grain, may be programmed into the instrument 11 by assigning a set of two numerals to each characteristic line. One numeral then represents the setting of the tap 19 of the potentiometer 18 which controls the slope of the characteristic line. The second numeral represents the setting of the tap 27 of the potentiometer 28 which controls shifting of the characteristic line parallel to itself. Depending upon the range of adjustment for each of the taps 19,27 and the number of settings within a respective range, the measuring instrument 11 may be programmed to at least approximate a large variety of characteristic lines.

The voltage of the calibrating voltage source 29 may be selected in dependence upon the voltage at the output of the logarithmic amplifier 13 and the possible output voltage at the tap 19 of the potentiometer 18. In other words, it is possible to select the calibrating voltage source 29 in such a manner that the output voltage of the potentiometer 28 may be increased as well as decreased about a central zero setting of the potentiometer 28. A characteristic line may then be shifted parallel to itself in both a negative and a positive direction. It is further possible to select the voltage of the calibrating voltage source 29 so that one of the terminal positions of the tap 27 of the potentiometer 28 constitutes a zero setting. In such an event, shifting of a characteristic line parallel to itself may be performed in a single direction only, that is, in either the positive direction or the negative direction. A further possibility, of course, is to select the voltage of the calibrating voltage source 29 in such a manner that the zero setting is located between the central position of the tap 27 and one of the terminal positions of the latter. Here, shifting of a characteristic line parallel to itself may again be performed in both the positive direction and the negative direction. However, the maximum possible displacement will be greater in one of these directions than in the other.

The taps 19,27 of the potentiometers 18,28 may be operable independently of one another. Alternatively, the taps 19,27 may be coupled to one another in a specific relationship so that a given displacement of one of the taps 19,27 causes the other of the taps 19,27 to move through a predetermined distance.

Figure 3:
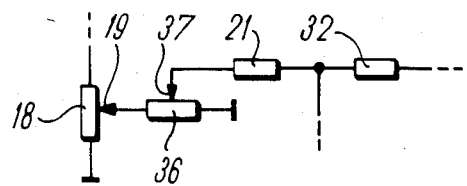
FIG. 3 illustrates another embodiment of a moisture measuring instrument in accordance with the invention.

FIG. 3 illustrates another embodiment of the moisture measuring instrument according to the invention.

The instrument of FIG. 3 differs from the instrument 11 of FIG. 1 in that the instrument of FIG. 3 is provided with temperature compensation means. This makes it possible to cancel out temperature as a factor in determining the moisture content of a material, e.g. the moisture content of wood in a drying oven may be determined independently of the existing temperature in the oven.

The temperature compensation means comprises an additional potentiometer or voltage adjusting device 36 having a tap 37. The potentiometer 36, which is grounded is disposed between the tap 19 of the potentiometer 18 and the resistor 21 connected with the inverting input 22 of the operational amplifier 23. The tap 19 of the potentiometer 18 is connected with a terminal of the potentiometer 36 while the resistor 21 is connected with the tap 37 of the potentiometer 36.

Except for the potentiometer 36, which constitutes part of the calibrating unit 20,23, the instrument of FIG. 3 is the same as the instrument 11 of FIG. 1. In particular, the instrument of FIG. 3 includes the elements 27–29 of the calibrating unit 20,23 which function to effect shifting of a characteristic line parallel to itself.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An instrument for measuring moisture content, particularly the moisture content of granular and non-granular solids including grain and wood, said instrument comprising:
   (a) a sensor for contacting a material undergoing moisture determination;
   (b) an indicator for indicating the moisture content of the material; and
   (c) a calibrating unit between said sensor and said indicator designed to calibrate said instrument for different materials, said calibrating unit including a calibrating voltage source, a summing device having output means connected with said indicator and input means, a first voltage adjusting device having a first input connected with said sensor and a first output connected with said input means, and a second voltage adjusting device having a second input connected with said calibrating voltage source and a second output connected with said input means.

2. The instrument of claim 1, wherein said voltage adjusting devices are operable from externally of said instrument.

3. The instrument of claim 1, wherein said sensor is designed to sense the electrical conductivity of the material.

4. The instrument of claim 1, comprising an amplifier between said sensor and said calibrating unit.

5. The instrument of claim 4, wherein said amplifier is a logarithmic amplifier.

6. The instrument of claim 1, wherein each of said voltage adjusting devices comprises a potentiometer.

7. The instrument of claim 1, wherein said summing device comprises an amplifier.

8. The instrument of claim 1, said sensor causing an input voltage to be generated at said first input during moisture determination; and wherein said calibrating unit is operative to effect adjustment of a characteristic line representing the electrical resistance of the material as a function of moisture content, said calibrating voltage source and said second voltage regulating device being designed to cause a shift of said characteristic line parallel to itself, and the direction and maximum amount of the shift being a function of the voltage of said calibrating voltage source and of the difference between said input voltage and the voltage of said calibrating voltage source.

9. The instrument of claim 1, wherein said summing device comprises an inverting operational amplifier having an inverting input which constitutes said input means.

10. The instrument of claim 1, wherein each of said voltage adjusting devices is operable independently.

11. The instrument of claim 1, wherein said voltage adjusting devices are operable as a unit.

12. The instrument of claim 1, wherein said calibrating unit comprises temperature compensation means.

13. The instrument of claim 12, wherein said temperature compensation means comprises an additional voltage adjusting device between said first voltage adjusting device and said summing device.

14. The instrument of claim 13, wherein said additional voltage adjusting device comprises a potentiometer.

15. The instrument of claim 1, wherein said calibrating voltage source is a d.c. voltage source.

16. The instrument of claim 1, comprising a measuring voltage source designed to supply said sensor with current for moisture determination.

17. The instrument of claim 16, wherein said measuring voltage source is a d.c. voltage source.

* * * * *